United States Patent [19]

Lewis

[11] 4,425,913
[45] Jan. 17, 1984

[54] SPLINT FOR USE WITH INTRAVENOUS LINE

[76] Inventor: Jamie B. Lewis, 28120 S. Ridgeforest Ct., Rancho Palos Verdes, Calif. 90274

[21] Appl. No.: 308,323

[22] Filed: Oct. 5, 1981

[51] Int. Cl.³ ............................................. A61M 5/00
[52] U.S. Cl. ............................ 128/133; 128/DIG. 6; 128/DIG. 26
[58] Field of Search ............ 128/133, 134, 165, 87 R, 128/215, 214 R, DIG. 6, DIG. 26, 89 R; 604/174, 179

[56] References Cited

U.S. PATENT DOCUMENTS

| | | | |
|---|---|---|---|
| D. 263,423 | 3/1982 | Aslanian | 128/133 X |
| 2,693,794 | 11/1954 | Neville | 128/DIG. 6 |
| 2,744,526 | 5/1956 | Saylors | 128/DIG. 6 |
| 3,295,518 | 1/1967 | Hazlewood et al. | 128/DIG. 6 |
| 3,423,095 | 1/1969 | Cox | 128/DIG. 6 |
| 3,590,817 | 7/1971 | Wresch | 128/133 |
| 3,722,508 | 3/1973 | Roberts | 128/DIG. 6 |
| 3,724,456 | 4/1973 | Waxman | 128/133 |
| 3,776,225 | 12/1973 | Lonardo | 128/87 R X |
| 3,812,851 | 5/1974 | Rodriquez | 128/DIG. 6 X |
| 4,191,180 | 3/1980 | Colley et al. | 128/DIG. 26 |

*Primary Examiner*—C. Fred Rosenbaum
*Assistant Examiner*—Michelle N. Lester
*Attorney, Agent, or Firm*—Nilsson, Robbins, Dalgarn, Berliner, Carson & Wurst

[57] ABSTRACT

A splint is disclosed for supporting the hand, wrist and at least a portion of the forearm during a time when a patient is connected to a lifeline, e.g. intravenous tube. The splint incorporates a substantially rigid molded body defining several shapes. Generally, a dome is provided for mating engagement with the palm of the hand and a transversely arcuate curved channel extends away from the dome to receive the wrist and a portion of the forearm. The contact surface is vented, as by a fabric covering, texture or perforations. The molded body further defines securing means for the lifeline, as in the form of rolled or beaded edges of the body which also add strength and rigidity. Fastening means for attaching the molded body to the hand, wrist and forearm are also incorporated in the form of straps fitted with fabric contact engaging means. A hole is defined in the molded body for tying it in a stable position.

1 Claim, 4 Drawing Figures

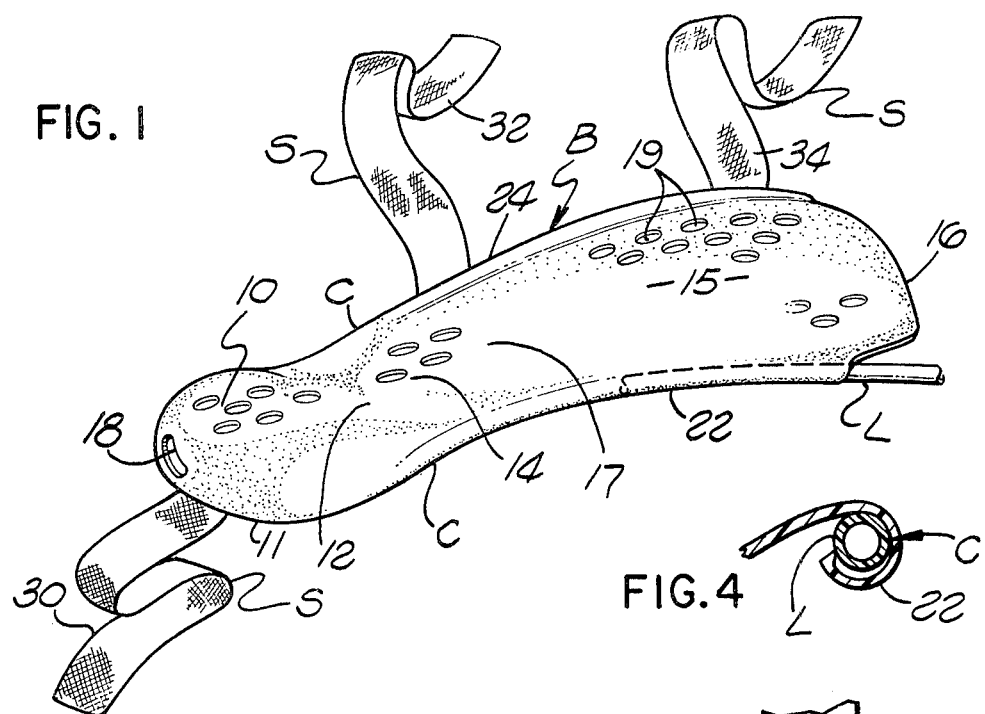
FIG. 1
FIG. 4
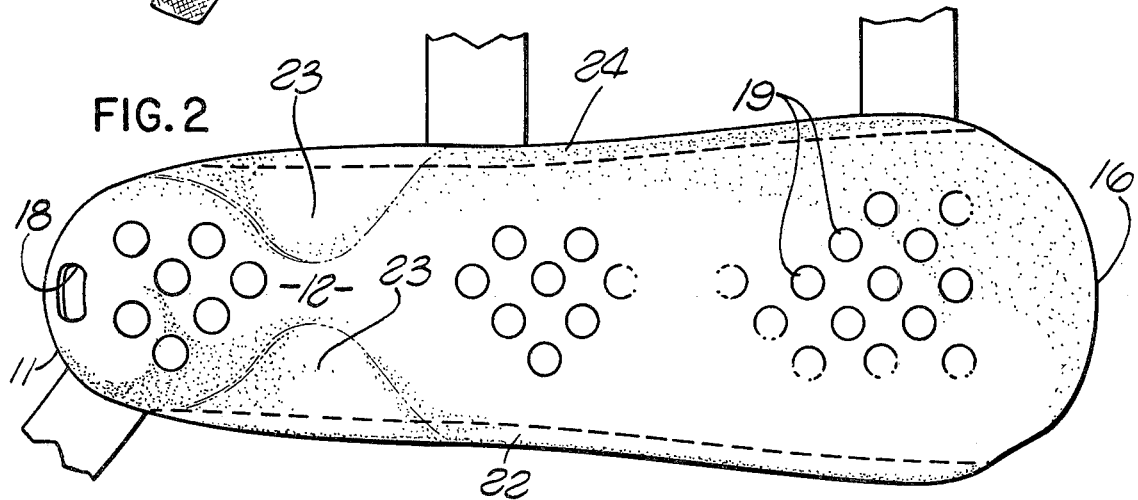
FIG. 2
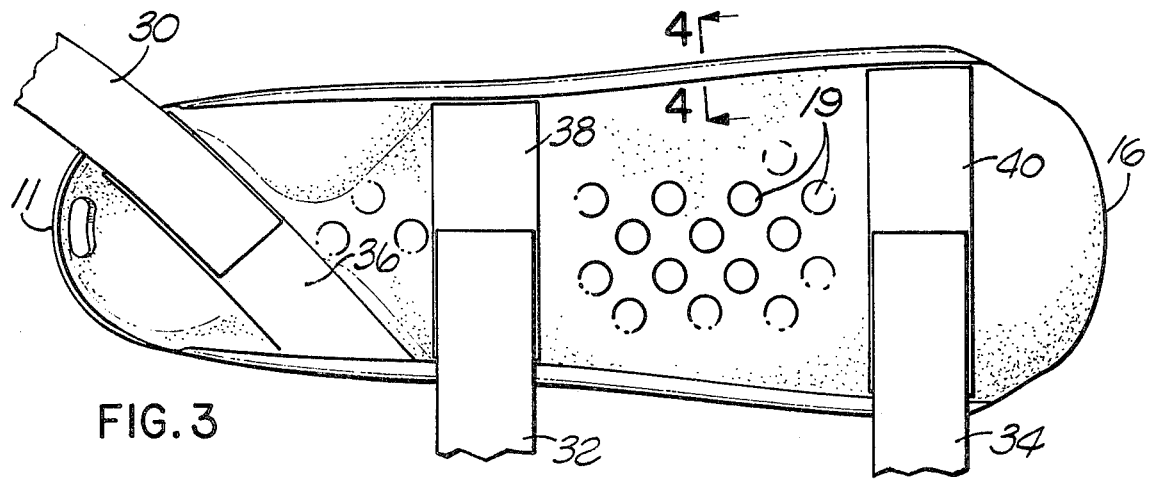
FIG. 3

SPLINT FOR USE WITH INTRAVENOUS LINE

BACKGROUND AND SUMMARY OF THE INVENTION

Each day, a multitude of people in various situations require intravenous fluid or drug therapy. The need to administer such therapy may arise for a patient in a convenient, stationary location, e.g. a hospital bed, or under extreme conditions as, for example, in an ambulance. Consequently, a continuing need exists for an economical, adaptable, convenient and effective apparatus for supporting an extremity for such therapy.

Currently, intravenous lifelines are secured to an extremity using a variety of different methods and techniques. According to the traditional technique, strips of tape are applied to attach a patient's forearm to a flat board ("arm board") with the objective of stabilizing the arm to receive and retain an intravenous line. Although that technique has been widely used for a number of years, it involves several distinct disadvantages. In general, the technique is time-consuming, sometimes difficult and often results in patient discomfort. Linelines set by the traditional technique often immobilize the patient in an unnatural position. Consequently, the lines are susceptible both to accidental disconnection and intentional removal, as by an irrational patient. Furthermore, the traditional technique requires substantial time to set the intravenous lifeline, and the time for starting or restarting may be critical. Still further, the use of adhesive tape in cooperation with various boards tends to abrade hair and skin in the contact areas and in some instances may cause serious adverse skin reactions.

In general, the present invention is directed to a somewhat rigid splint incorporating a molded body that is formed to mate with a person's hand, wrist and part of the forearm. The molded body has a textured surface and carries straps with contact fabric fasteners, (e.g. "Velcro") to be conveniently affixed in place. Lateral turned edges of the splint provide rigidity and afford grip channels for anchoring an intravenous line. An aperture is defined in the molded body for tying the splint in a fixed position.

BRIEF DESCRIPTION OF THE DRAWINGS

In the drawings, which constitute a part of this specification, an exemplary embodiment demonstrating the various objectives and features hereof is set forth as follows:

FIG. 1 is a perspective view of a splint constructed in accordance with the present invention;

FIG. 2 is a top plan view of the splint of FIG. 1;

FIG. 3 is a bottom view of the splint of FIG. 1; and

FIG. 4 is a fragmentary sectional view taken along the line 4—4 of FIG. 3.

DESCRIPTION OF THE ILLUSTRATIVE EMBODIMENT

As indicated above, a detailed illustrative embodiment of the invention is disclosed herein. However, embodiments may be constructed in accordance with various forms, some of which may be rather different from the disclosed illustrative embodiment. Consequently, the specific structural and functional details disclosed herein are merely representative, yet in that regard they are deemed to provide the best embodiment for purposes of disclosure and to provide a basis for the claims herein which define the scope of the present invention.

Referring initially to FIG. 1, a splint is illustrated in a perspective representation revealing a textured surface which will matingly engage a portion of the upper extremity extending from the palm of the hand to include part of the forearm. The splint incorporates a substantially rigid molded body B (carrying the textured contact surface) along with various attachment apparatus. Specifically, the splint includes straps S as indicated, for attachment to the upper extremity. Also, gripping channels C (FIG. 4) are provided at the lateral edges of the molded body B for anchoring an intravenous lifeline L.

In using the splint as illustrated in FIG. 1, the palm of a patient's hand is placed on a dome 10 at the left end of the molded body B (as depicted). The dome 10 gently tapers down (left) to an abrupt forward termination at a circular edge 11. On the other side, the dome 10 ends at a valley section 12 where a channel 14 extends back to an abrupt trailing edge 16 of the molded body B.

The channel 14 is transversely arcuate to define a cradle for the wrist and lower portion of the forearm. Along the dimension of its length, the channel 14 incorporates surface pad 15 with a gentle upward curve 17 for comfortable contact engagement with the hand and forearm. As illustrated, the surface of the body B is pierced by perforations 19.

At the forward base of the dome 10, just above the edge 11, a securing slot 18 is defined in the molded body B for tying the splint in a stable and secure position. For example, the splint may be secured to a bed, stretcher or wheelchair. Again, note that the forward edge 11 of the body B is not rolled but simply terminates as a somewhat hemispherical edge.

As the edge 11 approaches the wrist valley section 12, rolled or turned-edge channel closures 22 and 24 of somewhat cylindrical configuration extend along the length of the body B for gripping the lifeline L. The walls of the rolled channel closures 22 and 24 (FIGS. 2, 3 and 5) rigidify the molded body B which is relatively light and of somewhat uniform thickness. Also, a pair of indented sectors 23 (FIG. 2) of somewhat rounded triangular configuration provide dimensional rigidity at the wrist section 12. The sectors 23 may be of increased thickness or may simply take the form of indentations to provide reinforcement lines of strength.

The rolled channel closures 22 and 24 are for variously receiving a lifeline L (FIG. 4). Of course, any of a variety of arrangements may be used involving any of the channels depending upon the individual circumstances of the patient and the conditions attendant treatment.

The molded body B (FIG. 1) is to be physically attached to a patient by the straps S. In the illustrative embodiment, a hand strap 30 extends somewhat diagonally in relation to the dome 10 while a pair of forearm straps 32 and 34 extend laterally from the opposed side of the body, i.e., laterally from the edge 24. Aligned with each of the straps 30, 32, and 34 is a contact fastening member affixed to the underside of the body B. Specifically, referring to FIG. 3, contact fastener patches 35, 38, and 40 (e.g. "Velcro") are affixed in alignment with the straps 30, 32, and 34 respectively, the inside surfaces of which are contact-fastener surfaces. The straps and patches may be made of various fabric contact fastening materials, one form of which, as indicated above, is sold under the trademark "VEL-CRO".

It will be appreciated that a number of techniques and specifications might be employed in the manufacture of the splint of the present invention. However, the disclosed embodiment involves certain specific techniques and specifications. The molded body B (FIG. 1) is formed of lightweight semi-rigid white plastic, injection molded to the contoured configuration as described above. That is, the molded body B has a somewhat uniform thickness strengthened by the rolled edge channel closures 22 and 24 along with the sectors 23 (FIG. 2). In one practical embodiment, the total length of the body is 26.25 cm. with a width at the forearm channel 14 of 9.5 cm., a width at the wrist section 12 of 7.5 cm., and a width at the dome 10 of 6.5 cm. The dome 10 has a diameter of 5.0 cm and a depth of 2.0 cm. In conjunction with such dimensions, the body has a nominal thickness of approximately 2 mm., being substantially uniform.

Upon the completion of a molded body B, some minor trimming may be necessary, after which the surface contact pad 15 is secured to the upper surface (FIG. 2) of the body B. Of course, any of a variety of adhesive materials might be employed. Note that as alternatives the fabric or foam pad 15 can be eliminated or the pad surface 15 can be textured, as by stippling the upper surface of the body B to afford some ventilation in addition to the perforations 19 for the contacted skin areas.

The final step in the assembly of the splint simply involves attaching the contact fastener straps 30, 32, and 34 along with the patches 35, 38, and 40. Thereafter, the splint is ready for use. In that regard, it is to be noted that a few different sizes will generally be desirable to accommodate the physical dimensions of different people. In that regard, the illustrative embodiment as disclosed in detail above might be considered as a medium size from which variations may be made to accommodate the dimensions of smaller and larger persons.

One of the distinct advantages of the present invention resides in the ease of using the splint and the speed with which it can be set in place. Specifically, use of the splint simply involves fitting the body B onto the patient as described above then securing the body B in place with the contact straps 30, 32, and 34. Thereafter, an intravenous lifeline can be connected with the line L anchored in a channel C.

After a period of use, the splint is easily removed from a patient without the difficulties generally attendant the use of adhesive tape. In general, the disclosed embodiment is contemplated in a disposable form; however, clearly such a unit may be reused or a unit may be manufactured with some modifications rendering it more suitable for repeated use. In any event, it may be seen that the splint of the present invention affords a very useful, economical, convenient, safe, and comfortable structure for supporting the human hand in association with a lifeline. Of course, the apparatus can be implemented using a variety of different techniques and materials; and in that regard it is to be appreciated that the splint as represented herein is merely an illustrative embodiment deemed best for present purposes, however, recognizing that the scope hereof shall be in accordance with the claims and equivalents as set forth below.

What is claimed is:

1. A splint for supporting a patient's hand and at least a portion of the forearm to receive an intravenous line, comprising:

a substantially rigid, one-piece plastic body substantially symmetrical with reference to a center line and adapted to overlie the ventral aspect only of the patient's hand, wrist and forearm, and defining a dome for mating engagement with the palm only of the hand and a transversely arcuate channel extending away from said dome to receive said portion of the forearm, said dome disposed to support the hand in a substantially neutral position with regard to the forearm and terminating proximal the phalanges of the hand to permit free movement of the thumb and fingers thereon, the body defining edges turned to further rigidify the body, said edges each defining securing means in the form of grip sections for non-compressably receiving the intravenous line;

a plurality of ventilating apertures disposed through the dome; and fastener means for attaching the splint to the hand and forearm, said fastener means including a first strap disposed to retain the hand against the dome portion, a second strap disposed to retain the wrist against an intermediate portion of the splint, and a third strap disposed to retain the portion of the forearm against the transversely arcuate channel.

* * * * *